US 8,244,324 B2

(12) United States Patent
Atsumori et al.

(10) Patent No.: US 8,244,324 B2
(45) Date of Patent: Aug. 14, 2012

(54) OPTICAL MEASUREMENT INSTRUMENT FOR LIVING BODY

(75) Inventors: Hirokazu Atsumori, Kawagoe (JP); Masashi Kiguchi, Kawagoe (JP); Tadahiro Horita, Saitama (JP)

(73) Assignee: Hitachi, Ltd., Tokyo (JP)

( * ) Notice: Subject to any disclaimer, the term of this patent is extended or adjusted under 35 U.S.C. 154(b) by 1274 days.

(21) Appl. No.: 11/941,296

(22) Filed: Nov. 16, 2007

(65) Prior Publication Data

US 2008/0183056 A1    Jul. 31, 2008

(30) Foreign Application Priority Data

Jan. 25, 2007  (JP) .................................. 2007-014436

(51) Int. Cl.
*A61B 5/1455*   (2006.01)
(52) U.S. Cl. ........................ 600/310; 600/322
(58) Field of Classification Search .................. 600/310, 600/316, 318, 322, 323, 324, 326, 340, 473, 600/476
See application file for complete search history.

(56) References Cited

U.S. PATENT DOCUMENTS

| | | | | |
|---|---|---|---|---|
| 3,960,140 A | * | 6/1976 | Buxton .......................... | 600/519 |
| 4,819,752 A | * | 4/1989 | Zelin ............................. | 600/322 |
| 5,299,120 A | * | 3/1994 | Kaestle ......................... | 600/310 |
| 5,368,026 A | * | 11/1994 | Swedlow et al. ............. | 600/323 |
| 5,553,615 A | * | 9/1996 | Carim et al. .................. | 600/324 |
| 5,638,816 A | * | 6/1997 | Kiani-Azarbayjany et al. ............................. | 600/316 |
| 6,611,698 B1 | | 8/2003 | Yamashita et al. | |
| 6,816,241 B2 | | 11/2004 | Grubisic | |
| 2005/0272987 A1 | | 12/2005 | Kiani-Azarbayjany et al. | |

FOREIGN PATENT DOCUMENTS

| | | |
|---|---|---|
| EP | 1407711 | 4/2004 |
| JP | 05-93403 | 12/1993 |
| JP | 08-117209 | 5/1996 |
| JP | 9-098972 | 4/1997 |
| JP | 09-140715 | 6/1997 |
| JP | 9-149903 | 6/1997 |
| JP | 2000-116625 A | 4/2000 |
| JP | 2001-286449 | 10/2001 |
| JP | 2002-011012 | 1/2002 |
| JP | 2002-150123 | 5/2002 |
| JP | 2003-322612 | 11/2003 |
| JP | 2004-205493 | 7/2004 |
| JP | 2004-248961 | 9/2004 |

* cited by examiner

*Primary Examiner* — Eric Winakur
*Assistant Examiner* — Chu Chuan (JJ) Liu
(74) *Attorney, Agent, or Firm* — Mattingly & Malur, PC (57) ABSTRACT

An optical measurement instrument for a living body having an optical fiber removed, which is composed so as to transmit a driving signal for the light source to a plurality of an irradiation parts, as well as to convert a transmitted and received signal, between a processing and control unit and the probe unit, to a row of serial digital signals, by having one driving device for light source and one multiplexer, inside the probe unit.

11 Claims, 13 Drawing Sheets

OPTICAL MEASUREMENT INSTRUMENT FOR LIVING BODY

INCORPORATION BY REFERENCE

The present application claims priority from Japanese application JP2007-014436 filed on Jan. 25, 2007, the content of which is hereby incorporated by reference into this application.

BACKGROUND OF THE INVENTION

1. Field of the Invention

The present invention relates to a measurement instrument for information of the inside of a living body, using light.

2. Description of the Related Art

An instrument for measuring information of the inside of a living body, in a simple and convenient way without giving damage to the living body is used in a field such as clinical medical treatment or brain science or the like. Among these, in particular, a measurement method using light is a very effective tool. A first reason for that is that oxygen metabolism of the inside of a living body corresponds to a concentration of specific chromophores (such as hemoglobin, cytochrome aa3, myoglobin or the like), and the concentration of these chromophores can be determined by absorption amount of light. In addition, a second and a third reason for the optical measurement to be effective include the facts that light is simply and conveniently handled by an optical fiber, and furthermore, use thereof within a range of a safety standard does not give damage to the living body.

An optical measurement instrument for the living body for measuring the inside of a living body, by using light with a wavelength region from visible rays to infrared rays, by utilization of such advantages of the optical measurement, is described, for example, in Patent Document 1 or Patent Document 2. The optical measurement instruments for the living body described in these documents acquire the living body information such as blood circulation, hemodynamics, hemoglobin change or the like, from the detected light power, by emission of light by a semiconductor laser, introducing thus emitted light by an optical fiber to irradiate onto the subject, detecting light transmitting through or reflecting from the inside of the living body, and introducing the detected light by the optical fiber to a photodiode.

In addition, to realize such optical measurement for the living body, an optical measurement probe for the living body, where the optical fiber is contacted with the subject, is used: it is composed of the irradiation part for irradiating light, the light detection part for detecting light transmitting through or reflecting from the inside of the subject, and an immobilization member for immobilizing the irradiation part and the light detection part, by arranging them in a lattice way or a network way. In addition, this immobilization member has a shape so that the irradiation part and the light detection part are contacted with the subject, by using a band or a rubber string or a hair band or the like. As an example of this optical measurement probe for the living body, Patent Document 3 or the like is included. In addition, the optical fiber is usually present in plural, and the optical measurement probe for the living body, having a structure for bundling this plurality of optical fibers, is described in Patent Document 4, Patent Document 5, Patent Document 6, Patent Document 7, Patent Document 8, Patent Document 9 or the like.

In the above Patent Documents, the optical measurement is realized by introducing light emitted at the main body of the instrument to the living body via the optical fiber, however, it is desirable that the optical fiber is not used to realize more simple and convenient measurement and to reduce load to the subject. Conventional technologies realizing simple and convenient measurement by removing the optical fiber are described in Patent Document 10, Patent Document 11 or the like. They are technologies for acquiring living body information by wireless control, which are provided with a light source and a light receiver to the optical measurement probe for the living body.

Patent Document 1: JP-A-9-98972
Patent Document 2: JP-A-9-149903 (corresponding to US2001/0018554)
Patent Document 3: JP-A-8-117209
Patent Document 4: JP-A-2001-286449
Patent Document 5: JP-A-2002-11012
Patent Document 6: JP-A-2003-322612
Patent Document 7: JP-A-2004-205493 (corresponding to US2006/0058594)
Patent Document 8: JP-A-2004-248961
Patent Document 9: JP-A-5-93403
Patent Document 10: JP-A-9-140715
Patent Document 11: JP-A-2002-150123 (corresponding to US2003/0093361)

In the optical measurement for the living body, it is one of the most important problems to reduce load given to the living body to as low as possible. Contacting of the optical measurement probe for the living body which is composed of the optical fibers (hereafter referred to as a probe), with the living body as the subject, to realize the optical measurement for the living body, is considered to limit a movable range of the living body, depending on the length of the optical fiber, or to give load to the living body due to weight of the optical fiber. From such viewpoints, a compact and lightweight optical measurement instrument for the living body, without using the optical fiber has been required, to realize the optical measurement for the living body in a more natural state. Therefore, in the conventional technologies, the optical fiber is removed by arranging the light source and a detector on the inside of a probe, however, it requires installing of the driving device for the light source at a place connectable with the light source by an analog electric signal, which requires arrangement of the driving device for the light source on the inside of a probe, to suppress all electric or supposed noises to as low as possible. In addition, arrangement of a plurality of the light sources on the inside of a probe, to acquire multiple pieces of living body information, requires a plurality of driving devices for the light sources, resulting in increase in weight and volume thereof, and increase in load given to the subject. Accordingly, such a compact sized and lightweight optical measurement instrument for the living body has not been realized until now, that does not use the optical fiber and is capable of acquiring many pieces of living body information.

SUMMARY OF THE INVENTION

An optical measurement instrument for the living body is designed to have a probe unit for irradiating light onto a subject and detecting light transmitting through or reflecting from the inside of the subject; and a processing and control unit for transmitting and receiving a signal for light modulation and a received light signal from the probe unit, and acquiring a living body signal; and as the most simple constitution of the inside of the probe instrument, to arrange one or a plurality of irradiation parts for irradiating light; one or a plurality of light detection parts for detecting light transmitting through or reflecting from the inside of the subject; one driving device for a light source; and one multiplexer. By the arrangement of one multiplexer in the present constitution, it is capable of extremely reducing the weight of the probe unit, as well as providing compact sizing of the instrument, because only one driving device for the light source is required, even in the case where light is irradiated onto the living body from a plurality of the irradiation parts.

In addition, the present constitution is designed to install a digital-to-analog converter at the pre-stage of the driving device for the light source at the inside of the probe instrument, and an analog-to-digital converter and parallel-serial converter at the post-stage of the light detection part, and a digital signal is transmitted and received between the probe instrument and the processing and control unit. By transmitting and receiving an analog signal for light modulation and the received light signal inside of the probe instrument, noises can be suppressed, and also a plurality of the signals for light modulation and the received light signals are handled as a row of serial signals through parallel-serial conversion, and thus transmission and reception of signals between the probe unit and the processing and control unit can be realized by a simple constitution.

In addition, by arranging two or more multiplexers on the inside of a probe unit, light detection parts of at least two times the above constitution can be arranged, resulting in acquiring more living body information, while maintaining the effect of weight reduction. In addition, if necessary, by arranging two or more driving units for the light sources and the multiplexers corresponding thereto, inside the probe unit, many pieces of living body information can be acquired.

In addition, in the above constitution, light irradiated at each of the irradiation parts is emitted independently timewise, and is subjected to intensity modulation, and the received light signal is subjected to lock-in detection processing in the processing and control unit, by which noise such as disturbance light can be removed.

According to the optical measurement instrument for the living body in the present invention, it is possible to make a compact sized and lightweight instrument, and also acquire a high precision living body signal.

Other objects, features and advantages of the invention will become apparent from the following description of the embodiments of the invention taken in conjunction with the accompanying drawings.

DETAILED DESCRIPTION OF THE INVENTION

Explanation will be given below in detail of the present invention, with reference to embodiments of the invention and the drawings.

Embodiment 1

Figure 1:
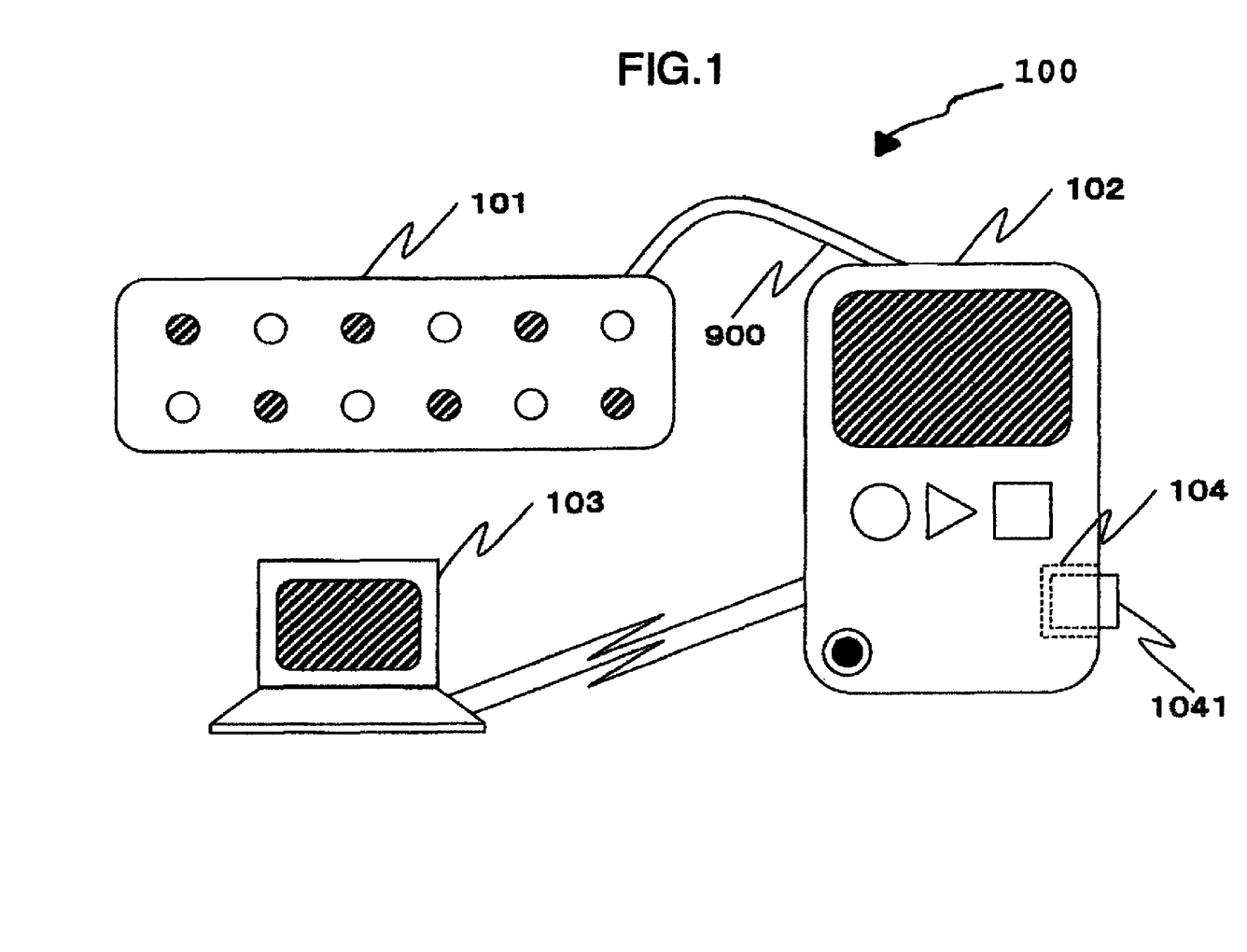
FIG. 1 is a schematic view of the optical measurement instrument for the living body in the present invention.

First of all, explanation will be given of a first embodiment of the optical measurement instrument for the living body according to the present invention. FIG. 1 is a schematic view showing a part of an instrument constitution of the optical measurement instrument for the living body according to the present invention. The optical measurement instrument 100 for the living body is composed of a probe unit 101, a processing unit 102, a cable 900 for transmitting a signal between the probe unit 101 and the processing unit 102, and a control unit 103: and by a wireless transceiver 1021 (not shown) of the processing unit 102, and by a wireless transceiver 1031 (not shown) of the control unit 103, the driving signal for a light source and received light signal at the probe unit 101 and the processing unit 102 are controlled so as to enable the optical measurement for the living body. Signal communication between the processing unit 102 and the control unit 103 is not necessarily made by the wireless method, and may be carried out by wired signal transmission using a cable, and furthermore, the processing unit 102 and the control unit 103 are not necessarily separated, and may be set as a one-piece constitution. In addition, the processing unit 102 is provided with a recording part 104 for recording measurement data or measurement procedures, and by detaching an external memory 1041 to the recording part 104, taking out the recorded data or reading out the measurement procedures recorded in advance can be carried out. By control of measurement according to the measurement procedures recorded in advance by the recording part 104 and the external memory 1041, and as well by recording the measured data into the external memory 1041 at the recording part 104, measurement is possible using only the probe unit 101 and the processing unit 102, without using the control unit 103. Here, description will be made of measurement using only the probe unit 101 and the processing unit 102.

Figure 2:
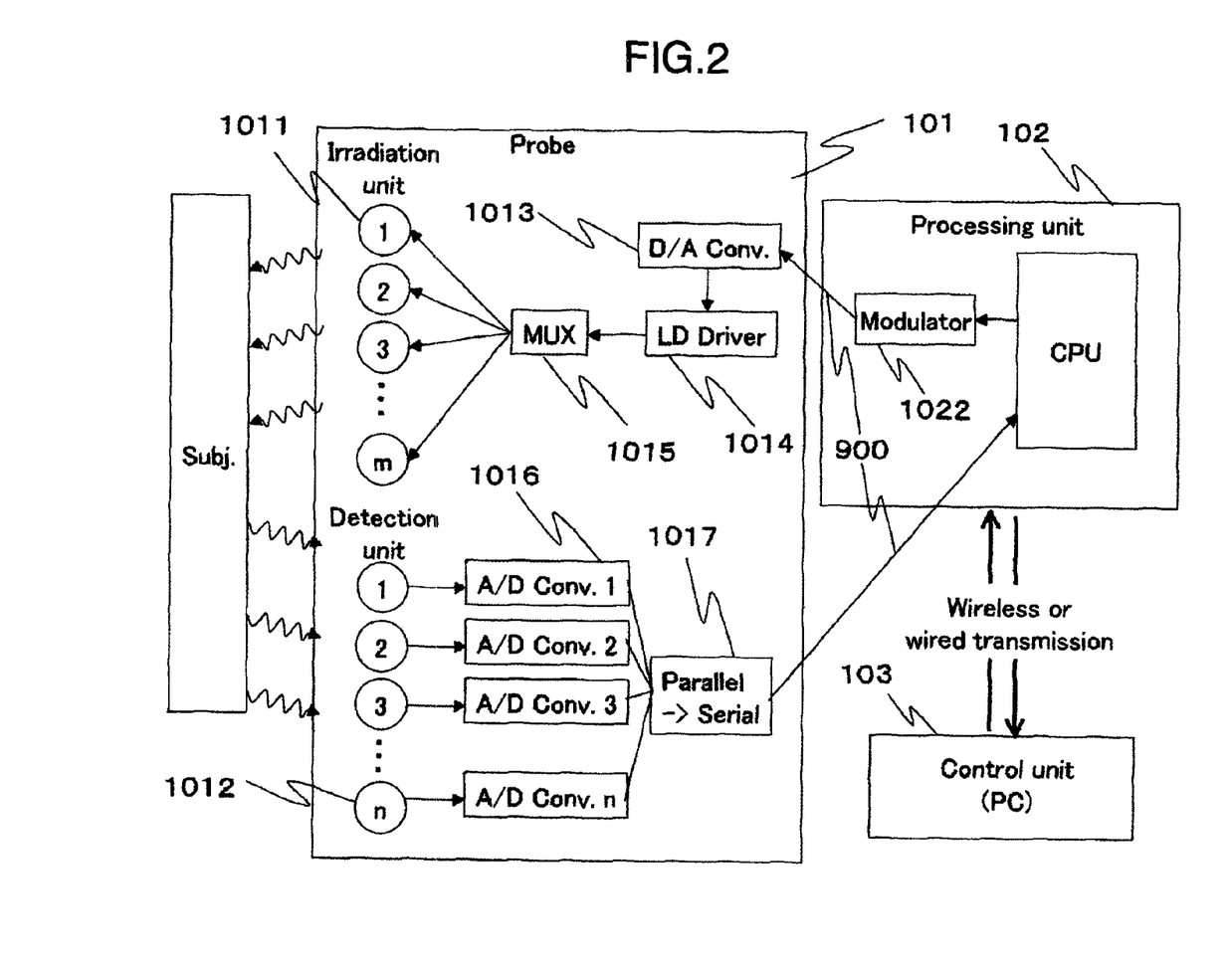
FIG. 2 is a schematic view showing signal flow, in the optical measurement instrument for the living body in the present invention.
Figure 6:
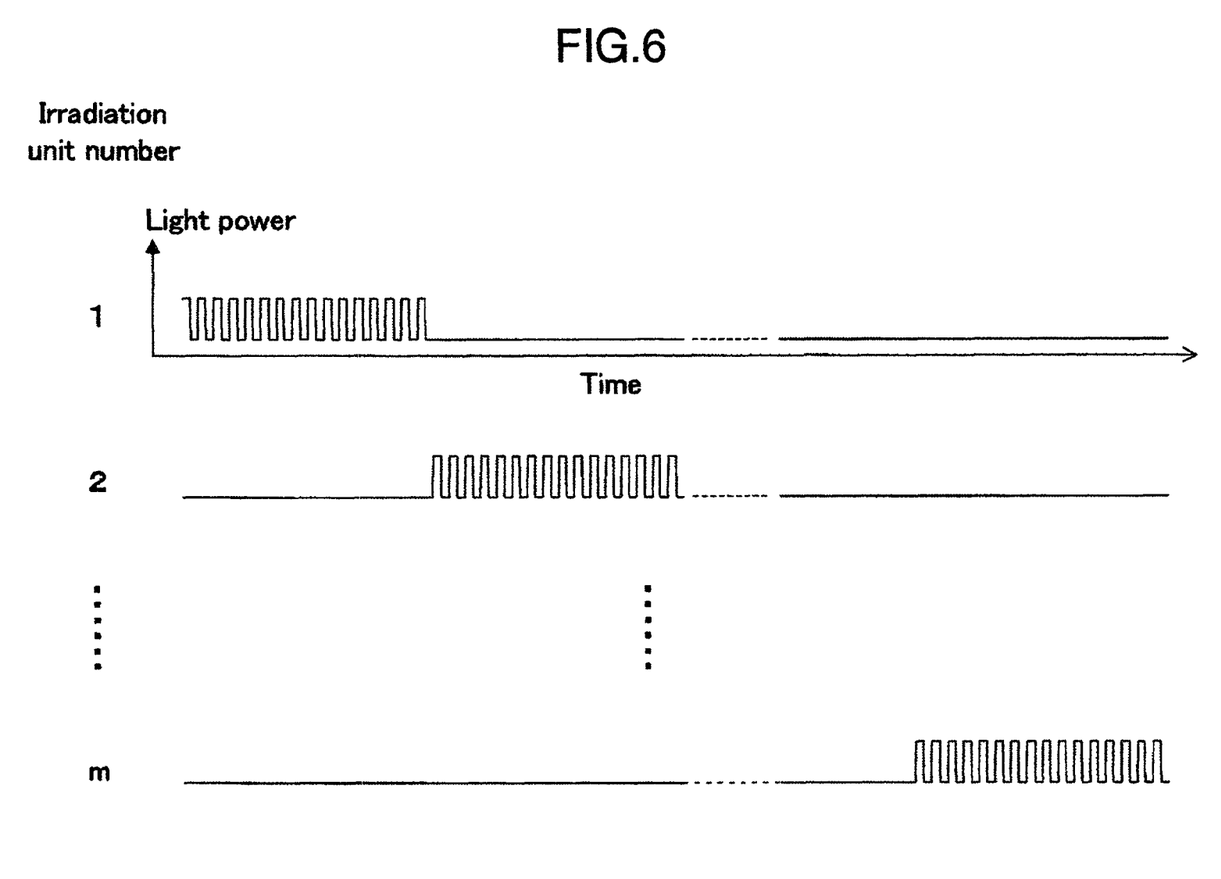
FIG. 6 is a conceptual drawing showing that lights irradiated at a plurality of irradiation parts have the same modulation frequency, and irradiation timing thereof at each of the irradiation parts is not overlapped timewise, in the optical measurement instrument for the living body in the present invention.

FIG. 2 shows outline of signal flow in the instrument constitution shown in FIG. 1. The probe unit 101 is provided with one or a plurality of the irradiation parts 1011 for irradiating light onto the living body, and one or a plurality of light detection parts 1012 for detecting irradiated light transmitting through or reflecting from the living body. According to the present invention, a driving signal for a light source at the irradiation parts 1011 is generated as a digital signal for amplitude modulation at a certain specific frequency or based on a certain kind of code at a modulator 1022 present inside the processing unit 102, and transmitted to the probe unit 101. The driving signal for a light source is converted to an analog signal for amplitude modulation by a digital-to-analog converter 1013 in the probe unit 101, and transmitted to one driving device for a light source 1014. In the driving device for a light source 1014, the analog signal for amplitude modulation is converted to the driving signal for a light source, and transmitted to one or each of a plurality of the irradiation parts 1011, by the multiplexer 1015, with a timing shifted as shown in FIG. 6. In the irradiation parts 1011, intensity-modulated light is emitted, based on the driving signal for a light source, and sequentially irradiated onto the living body. In the light detection parts 1012, the intensity-modulated light, transmitting through or reflecting from the living body, is output as analog signals for amplitude modulation. These analog signals for amplitude modulation are converted to digital signals for amplitude modulation in an analog-to-digital converter 1016 corresponding to each of the light detection parts 1012. The resulting digital signals for amplitude modulation are assembled into one signal by a parallel-serial converter 1017, and transmitted to the processing unit 102 as one digital signal. In this way, by having the digital-to-analog converter 1013, the driving device for a light source 1014, the multiplexer 1015, the analog-digital converters 1016 and the parallel-serial converter 1017 on the inside of a probe unit 101, signal communication at a light source drive side and a light detection side can be transmitted between the probe unit 101 and the processing unit 102, by each one cable.

According to the optical measurement instrument for the living body by the present invention, light irradiation from all of the irradiation parts 1011 becomes possible by using the multiplexer 1015. Therefore, it is not necessary to prepare driving devices for light sources corresponding to each of the irradiation parts 1011, and thus use of only one driving device for a light source 1014 is sufficient: this instrument constitution is essential in compact sizing of the instrument.

Embodiment 2

Figure 3:
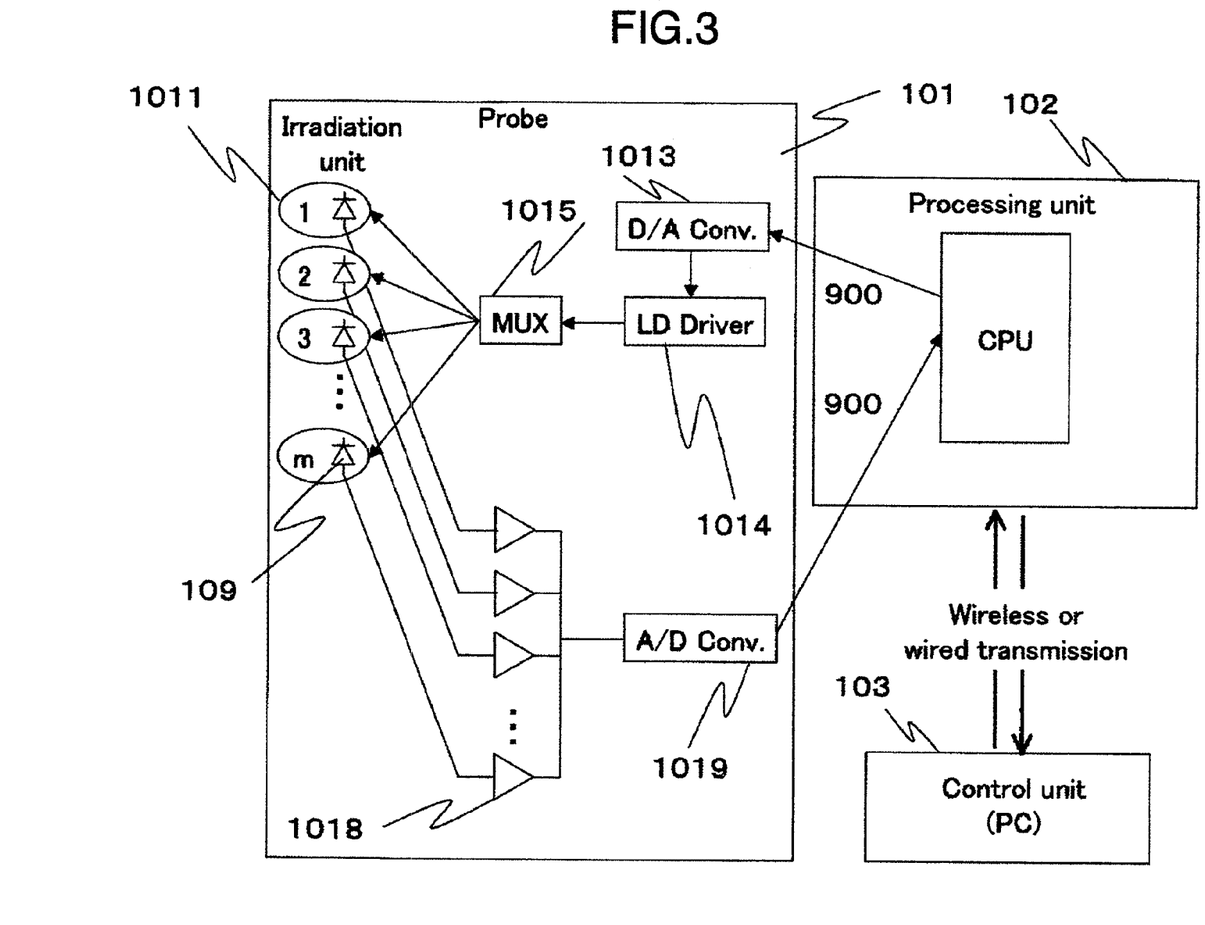
FIG. 3 is a schematic view showing signal flow, in the optical measurement instrument for the living body in the present invention.

Explanation will be given of an example for correcting the detected light power, in the case where the irradiated light power varies by various causes including temperature change of the living body or surrounding area or the like. FIG. 3 shows one embodiment in the present invention, and the light detection parts 1012, the analog-digital converters 1016 and the parallel-serial converter 1017, inside the probe unit 101, are omitted here. According to the present embodiment, each of the irradiation parts 1011 is provided with a monitor photodiode 109 to always detect the irradiated light power, and assemble the detected signals into one through a buffer memory 1018, transmit to an analog-digital converter 1019, and transmit to the processing unit 102, as a series of digital signals. In addition, all of the above processing to the transmission to this processing unit 102 may be carried out by using the analog-to-digital converter and the parallel-serial converter corresponding to the light detection parts 1012, similarly as in the constitution shown in FIG. 2. When a light power to be irradiated originally is represented as Ps, and a practically irradiated light power at a certain time t changes to k(t) times the original level, by various causes such as temperature change of the surrounding area or the like, the practically irradiated light power at a certain time t becomes Ps×k(t). In this case, the irradiated light power of Ps×k(t), monitored by the monitor photodiode 109, is transmitted to the processing unit 102, and k(t) can be calculated by a known value Ps. On the other hand, when the detected light power to be detected originally by the light detection parts 1012 is represented as Pd(t) for the light power Ps to be irradiated originally, Pd(t) contains time variation of living body information obtained by light, transmitting through or reflecting from the inside of the living body, as the subject. Therefore, in the case where time variation k(t) is generated in the irradiated light power, the detected light power becomes Pd(t)×k(t), and is detected as containing both of the time variation of the living body information and the time variation of the irradiated light power. Here, because the time variation k(t) of the irradiated light power is acquired in advance by the monitor photodiodes 109 and the processing unit 102, the original signal Pd(t) can be recovered by dividing the detected light power with k(t), in any of real time processing or post-processing, by which measurement data of the living body information can be recorded, not affected by the irradiated light power changes accompanied by various causes such as temperature change of the surrounding area or the like.

In addition, when the driving signal for a light source is represented as V(t), and by feedback of the resulting k(t) to the driving signal for a light source in real time, the irradiated light power can also be adjusted. Namely, by using k(t−1) obtained just before, at a certain time t, V(t)+k(t−1) may be transmitted as the driving signal for a light source. In this way, light intensity emitted at the irradiation part can be maintained nearly constant.

Embodiment 3

Figure 4:
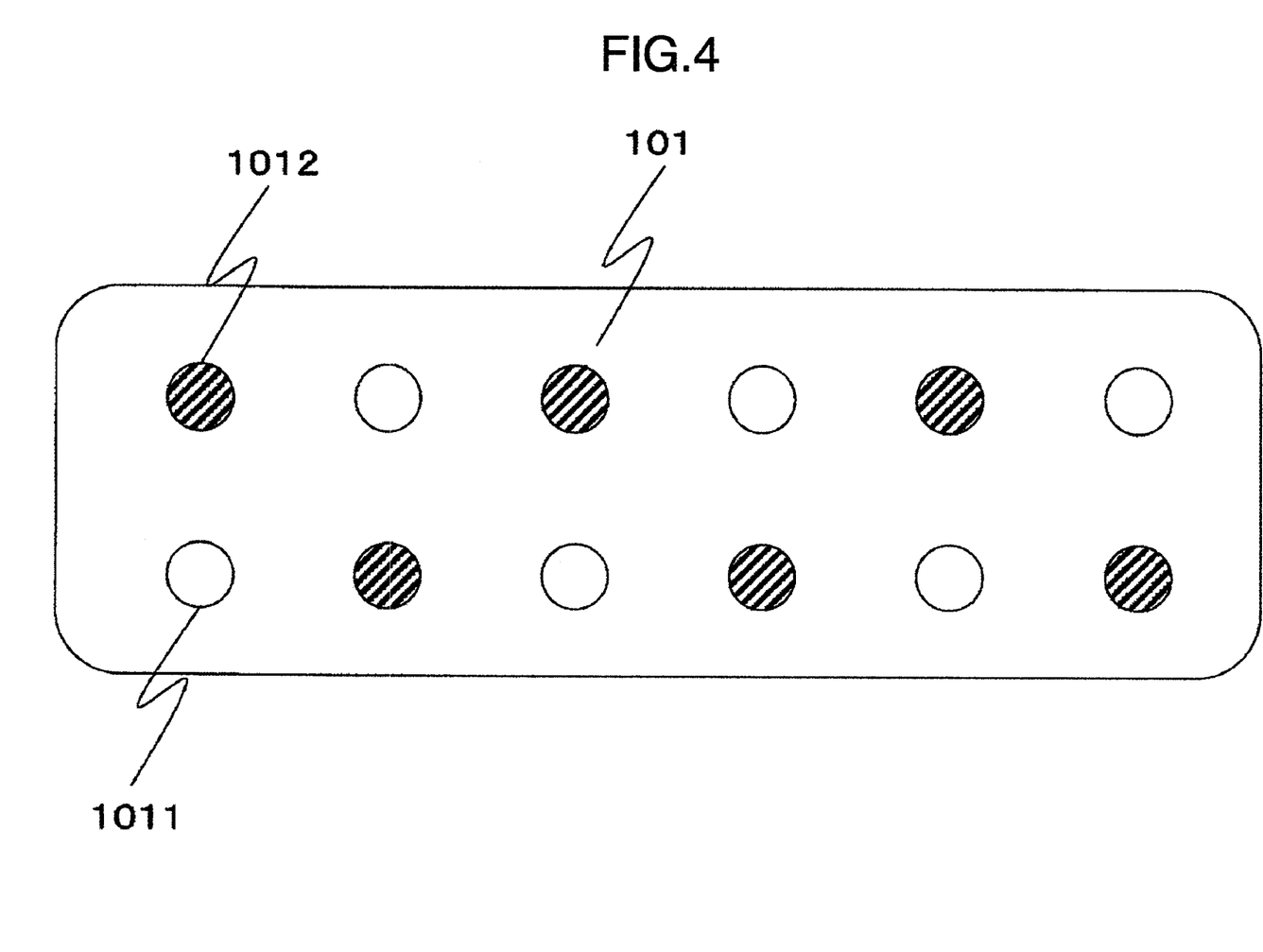
FIG. 4 is a schematic view showing an example of irradiation parts and light detection parts, in the optical measurement instrument for the living body in the present invention.

FIG. 4 shows one embodiment in the present invention, and shows the irradiation parts 1011 and the light detection parts 1012 arranged in the probe unit 101. In this arrangement, each of the light detection parts 1012 detects light irradiated by a plurality of the irradiation parts 1011, and in this case, because the light irradiation by the irradiation parts 1011 is separated timewise, by the multiplexer 1015 in FIG. 2, each of the signals from any of the irradiation parts 1011 can be separated, based on irradiation timing processed in the processing unit 102. In addition, according to the optical measurement instrument for the living body by the present invention, because irradiated light by each of the irradiation parts 1011 is intensity modulated light, and is subjected to lock-in detection processing in the processing unit 102, generated noise caused by various reasons such as stray light or the like coming into the light detection parts 1012 can be removed and thus the original living body signal can be acquired in good precision.

Embodiment 4

Figure 5:
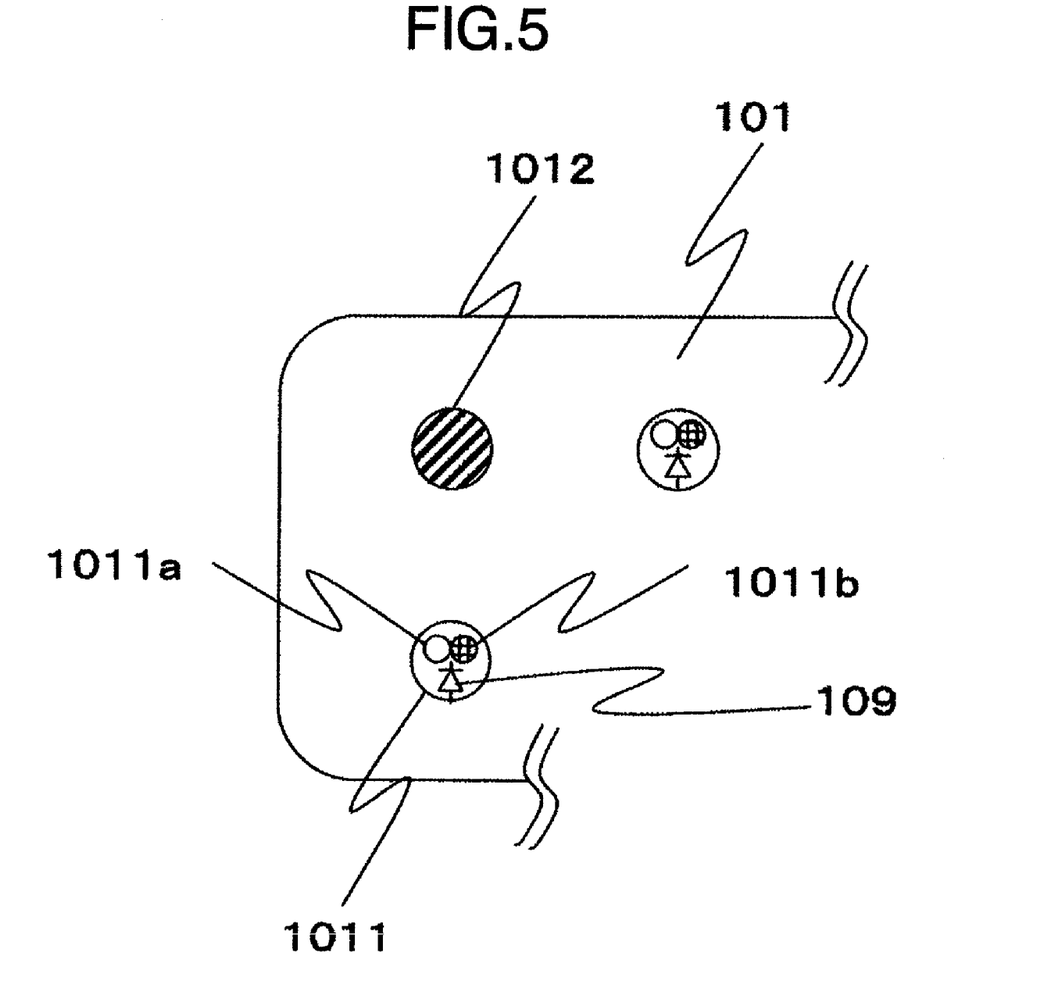
FIG. 5 is a schematic view showing an example provided with two irradiation parts, having two light sources of different wavelengths and one monitor photodiode, at the vicinity of one light detection part, in the optical measurement instrument for the living body in the present invention.

In the present embodiment, explanation will be given of an example of efficient setting of a detection range of the analogto-digital converters 1016, by adjusting a light power level from a plurality of the irradiation parts 1011, detected by the light detection parts 1012, as setting of the light power level of the irradiation parts 1011 in the optical measurement for the living body. In the example shown in FIG. 5, each of the irradiation parts 1011 is provided with a light source 1011a of a wavelength of λ1 and a light source 1011b of a wavelength of λ2, different from λ1, and the monitor photodiode 109 for monitoring light intensity of these two light sources, and in the light detection parts 1012, four lights arrive from at least two irradiation parts 1011. In this case, the four detected light powers of light arrived to the light detection parts 1012 are represented as P1, P2, P3 and P4 (level of the light power is in the order of P1<P2<P3<P4). Because they are based on light irradiated separately timewise by the multiplexer 1015, the light power can be evaluated independently. In the case where P1, P2 and P3 are weaker relative to P4, the irradiated light power can be adjusted by matching with the detected light power levels by giving feedback so as to make each of the driving signals for the light sources (P4/P1) times, (P4/P2) times, and (P4/P3) times, in the processing unit 102. On the other hand, because it is required to secure safety of the irradiated light power, a safety standard level Pb has been set in advance to control, in the processing unit 102, so that the irradiated light power, detected at the monitor photodiode 109, does not exceed Pb. For example, in the above example, in the case where the irradiated light powers of four light sources are represented by Ps1, Ps2, Ps3, and Ps4, and provided that Ps2<Pb<Ps3, feedback is given to the driving signal for a light source in the processing unit 102, so as to make each of the irradiated light powers (Pb/Ps1) times, (Pb/Ps2) times, (Pb/Ps3) and (Pb/Ps4) times.

Embodiment 5

Figure 7:
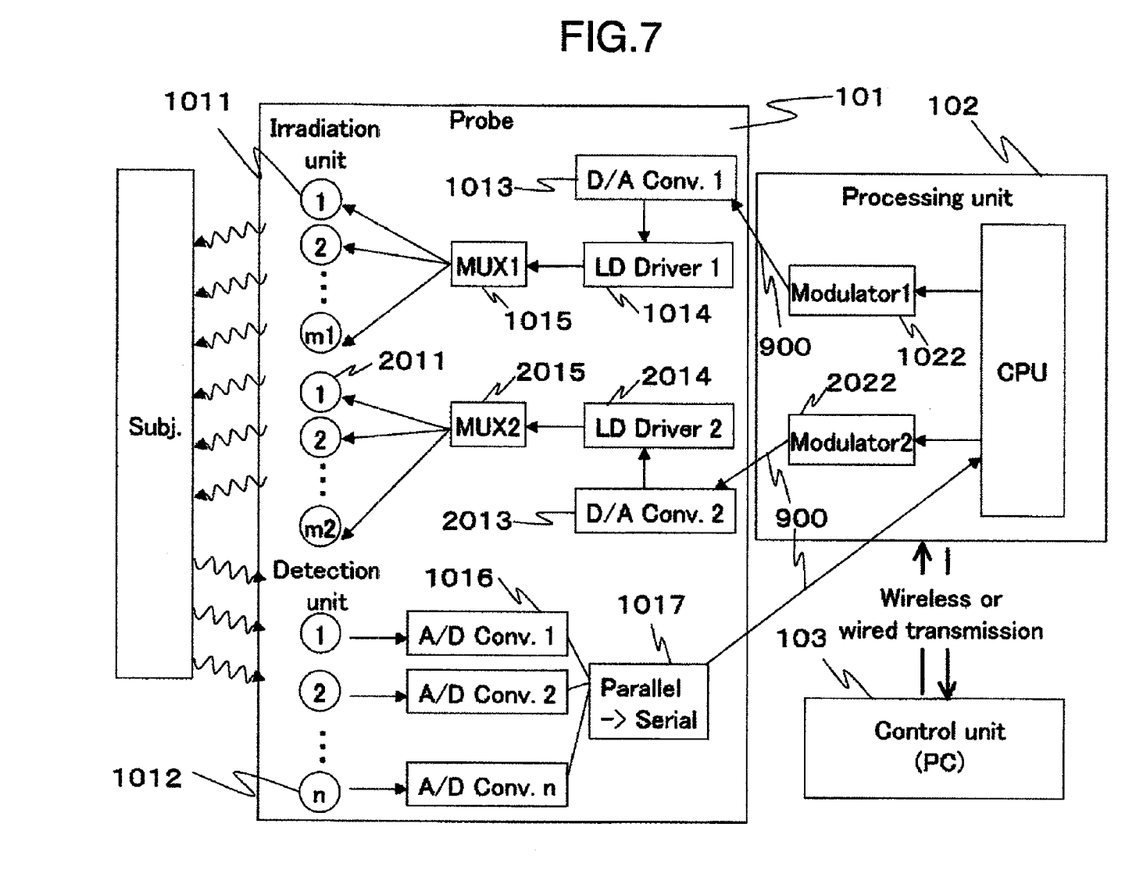
FIG. 7 is a constitution example that realizes acquiring many measurement signals, by utilization of a driving signal for a light source, having two different modulation frequencies, in the optical measurement instrument for the living body in the present invention.

Then, explanation will be given of an embodiment composing the optical measurement instrument for the living body, having the irradiation parts 1011 with a number of at least two, by using two modulators, two digital-to-analog converters, two driving devices for light sources and two multiplexers, and not changing irradiation time of all the irradiation parts 1011. Namely, as shown in FIG. 7, in the first modulator 1022 provided at the processing unit 102, a digital signal for amplitude modulation, based on a first modulation frequency or a first code, is emitted, which is transmitted to the first digital-analog converter 1013 via the cable 900; based on this, a first driving signal for a light source is emitted in the first driving device for a light source 1014, which is transmitted to the first multiplexer 1015; the first driving signal for a light source is distributed to the m1 irradiation parts 1011 by the first multiplexer 1015, to irradiate light on the subject, as well as, in the second modulator 2022 provided at the processing unit 102, a digital signal for amplitude modulation, based on a second modulation frequency without correlation to the first modulation frequency, or a second code without correlation to the first code, is emitted, which is transmitted to the second digital-analog converter 2013 via the cable 900; based on this, a second driving signal for a light source is emitted in the second driving device 2014 for a light source, which is transmitted to the second multiplexer 2015; and the second driving signal for a light source is distributed to the m2 irradiation parts 2011 by the second multiplexer 2015, to irradiate light on the subject. In this case, in the irradiation parts 1011 and the irradiation parts 2011, light having the first modulation frequency or the first code, and light having the second modulation frequency or the second code are irradiated on the subject at the same time, however, because light signals, having different frequencies or codes as compared with a target, are removed by the lock-in detection processing carried out in the processing unit 102, more living body information can be acquired without being affected by light signals having the different frequencies or codes, and in addition without deteriorating precision for noise and measurement time.

Embodiment 6

Figure 8:
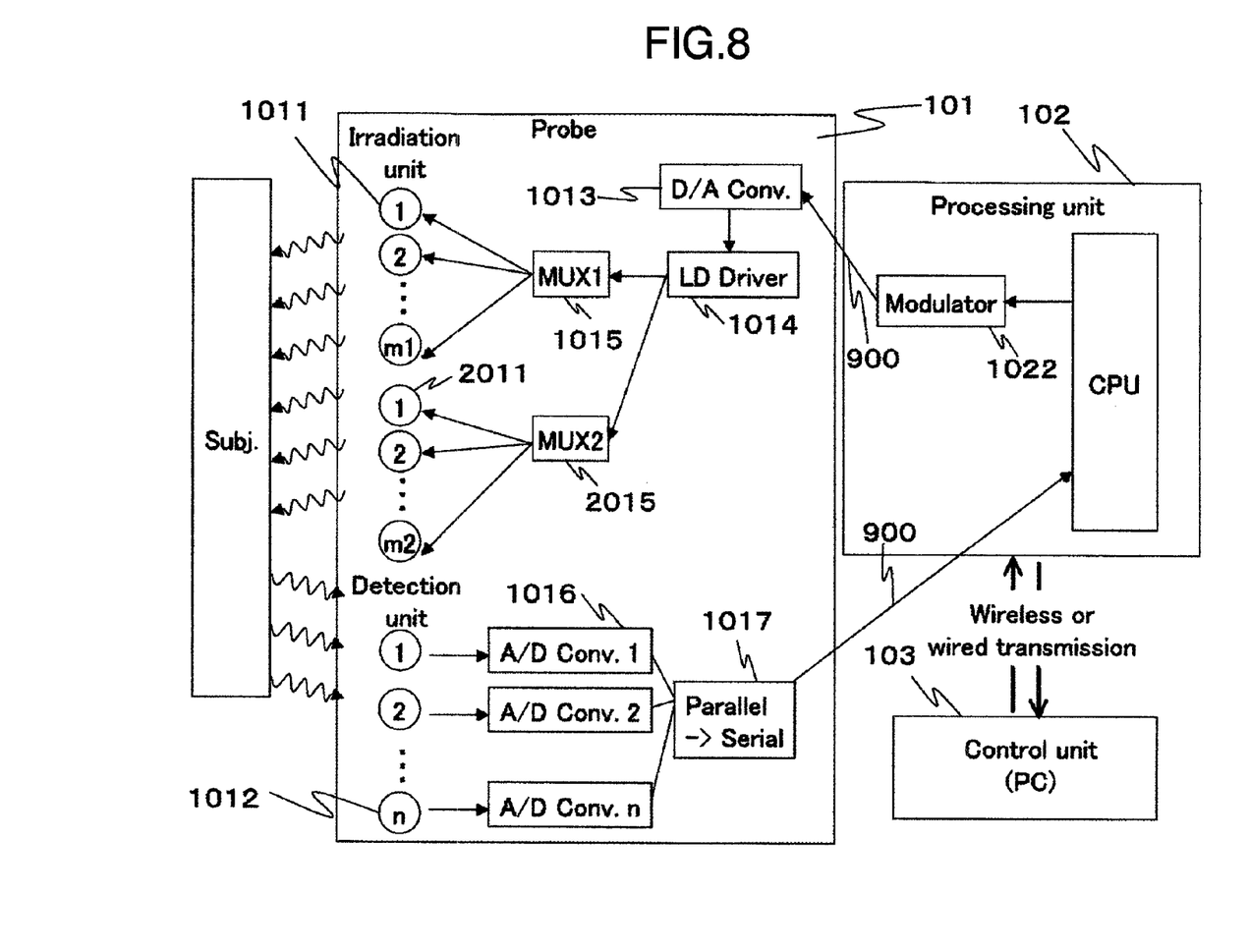
FIG. 8 is a constitution example that realizes acquiring many measurement signals, by the driving signal for a light source, having one modulation frequency, in the optical measurement instrument for the living body in the present invention.

In the example shown in the above embodiment 5, in the case where the irradiation parts 1011 to which is distributed the driving signal for a light source by the first multiplexer 1015, and the irradiation parts 2011 to which is distributed the driving signal for a light source by the second multiplexer 2015 are sufficiently apart in space, and irradiated light by the one irradiation parts 1011 is propagated inside the subject, and judged to be attenuated to such a degree as to be negligible at the vicinity of the other irradiation parts 2011, it is possible to set the first modulation frequency or the first code, and the second modulation frequency or the second code to the same. In this case, as shown in FIG. 8, by providing the first multiplexer 1015 and the second multiplexer 2015, as well as each of only one modulator 1022, digital-to-analog converter 1013 and driving device for a light source 1014, many pieces of living body information can be acquired by a more simplified instrument constitution. In addition, by combination of the constitution by the present embodiment and the instrument constitution shown in the embodiment 5, more pieces of living body information can be acquired.

Embodiment 7

Figure 9:
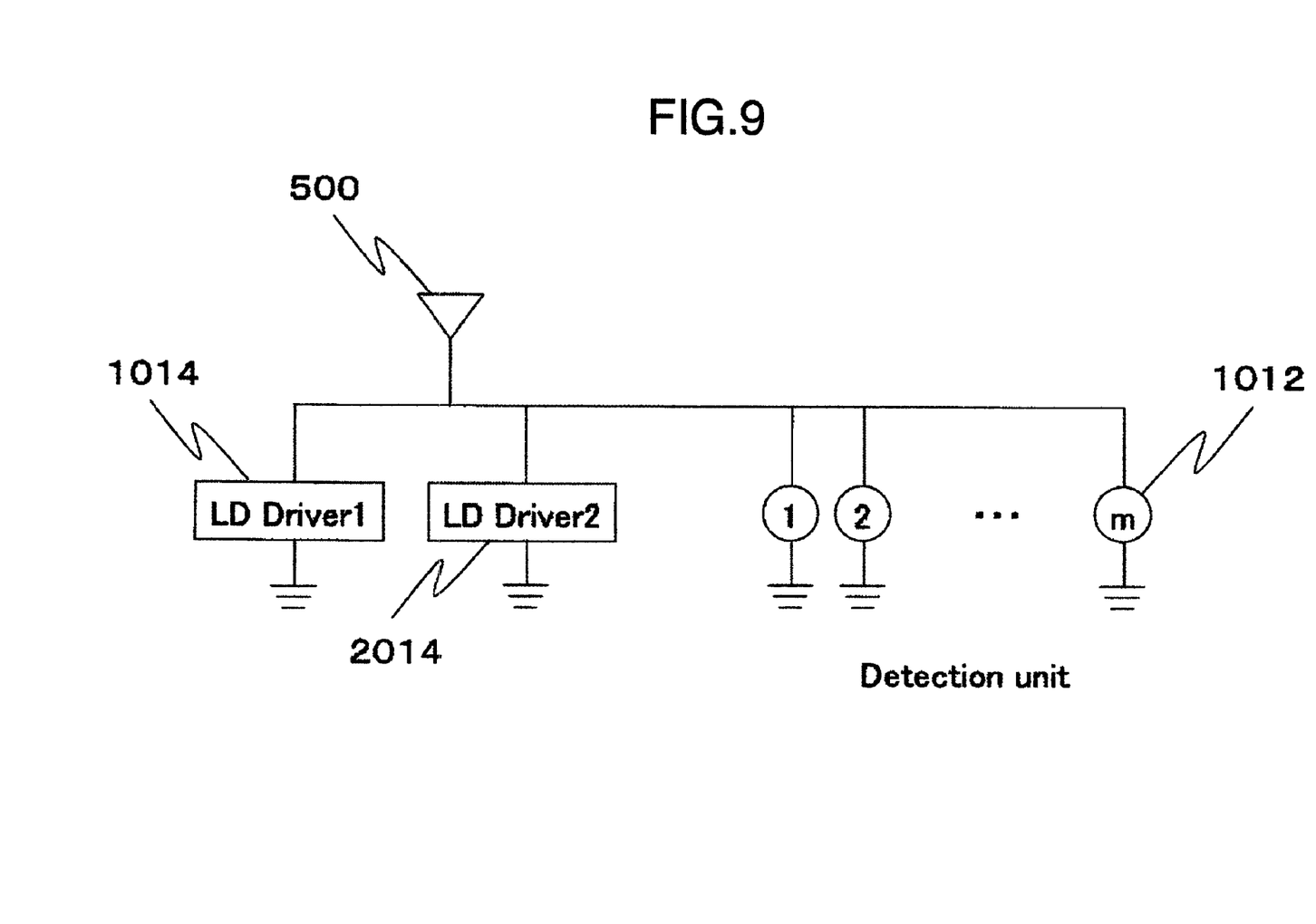
FIG. 9 is a constitution example for supplying a power source to a driving device for a light source and the light detection part.
Figure 10:
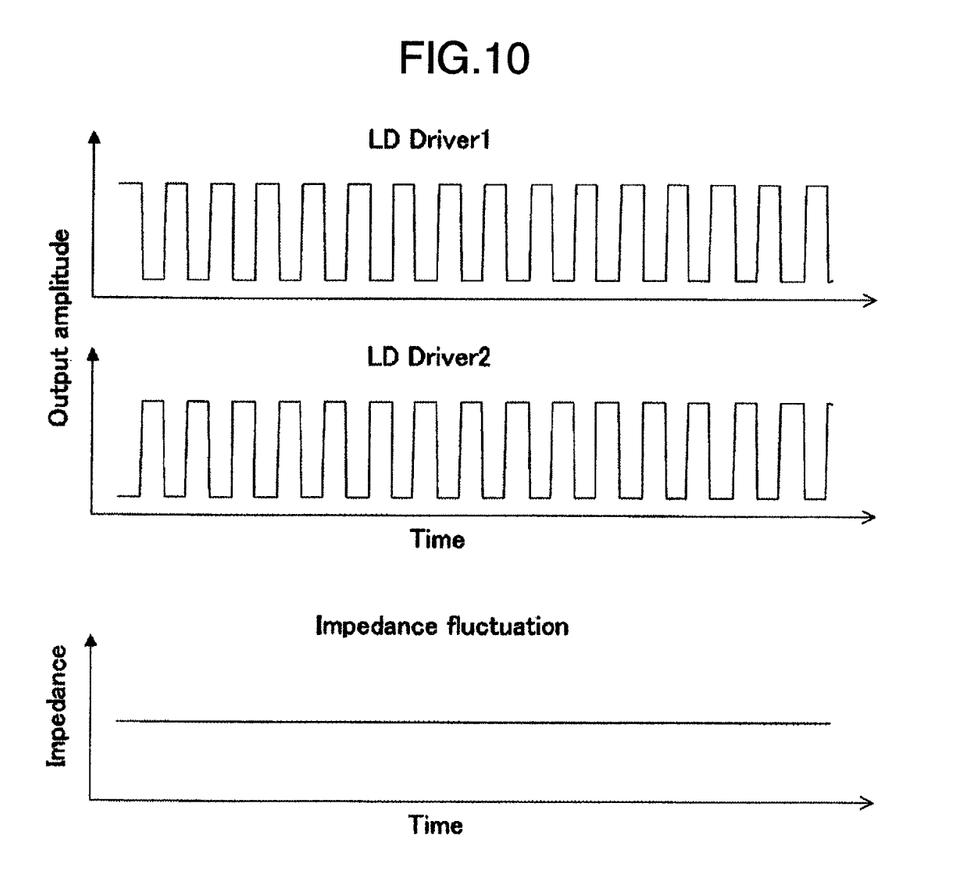
FIG. 10 is an example of signal amplitude change when the same frequency is provided to the driving signal for a light source, emitted by two driving devices for a light source, and when phases thereof are inverted, and impedance change generating in this case.

In addition, in the instrument constitutions of the above embodiment 5 and the embodiment 6, by inverting a phase of the driving signal for a light source emitted by each of the first driving device for a light source and the second driving device for a light source, noise derived from the power source can be suppressed. As shown in FIG. 9, in a state that the first driving device 1014 for a light source, the second driving device for a light source 2014 and the light detection parts 1012 are supplied power from the same power source part 500, and in the case where the analog driving signal for a light source, which is output from the first driving device for a light source 1014 and the second driving device for a light source 2014, is subjected to amplitude modulation in a rectangular wave by a certain specific frequency, impedance fluctuation is generated with amplitude modulation viewed from the power source part 500. Therefore, it may be possible for the fluctuation with the modulation to enter the light detection parts 1012 as noise. In this case, when the first driving signal for a light source emitted from the first driving device 1014 for a light source, and the second driving signal for a light source emitted from the second driving device 2014 for a light source are rectangular waves modulated by the same frequency, and the phases thereof are inverted, as shown in FIG. 10, impedance fluctuation viewed from the power source part 500 becomes nearly constant. In the optical measurement instrument for the living body according to the present invention, unnecessary noise can be suppressed by using the above first and second driving signals for light sources.

Embodiment 8

Figure 11:
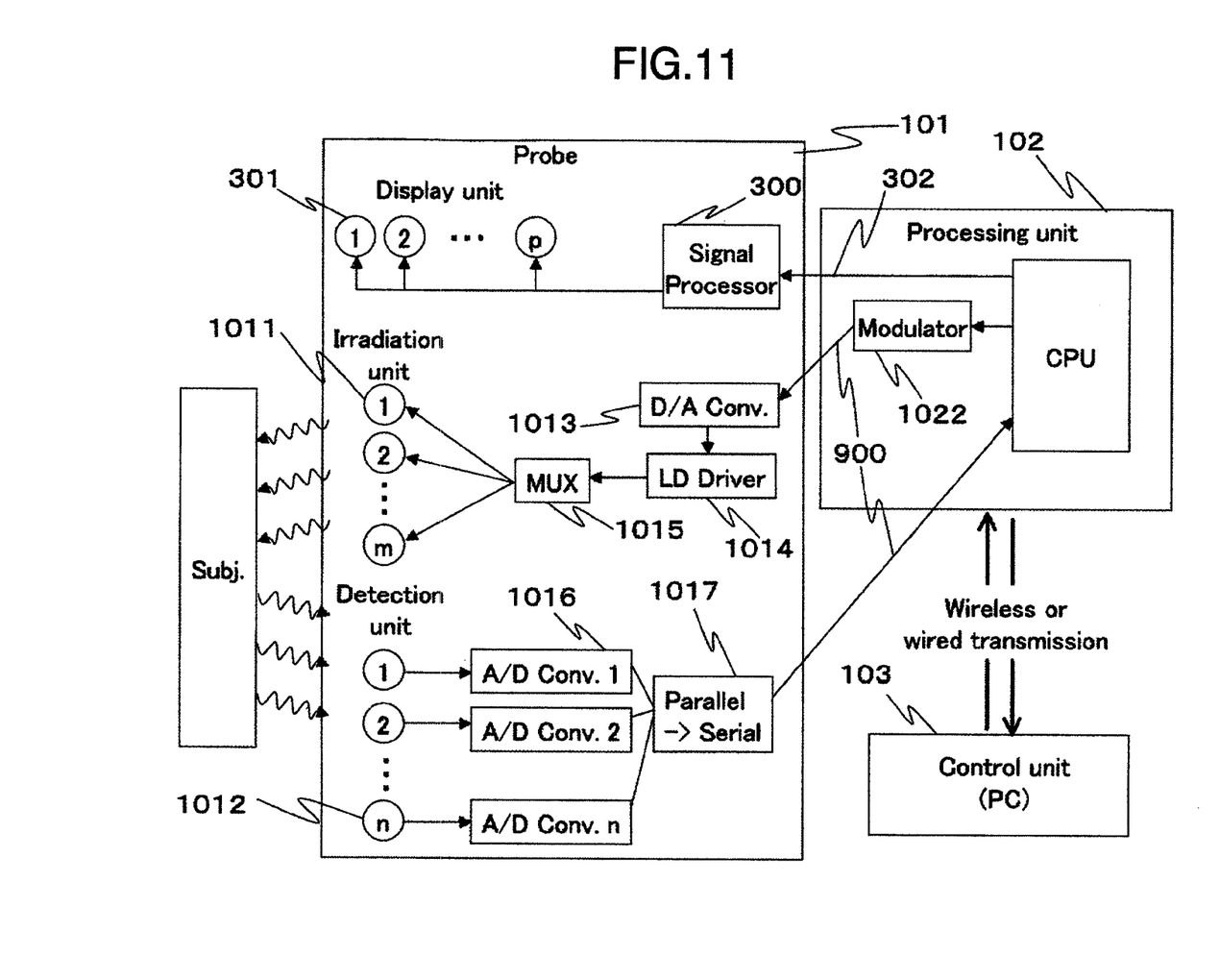
FIG. 11 is a constitution example for displaying living body information on a display part, in the optical measurement instrument for the living body in the present invention.
Figure 12:
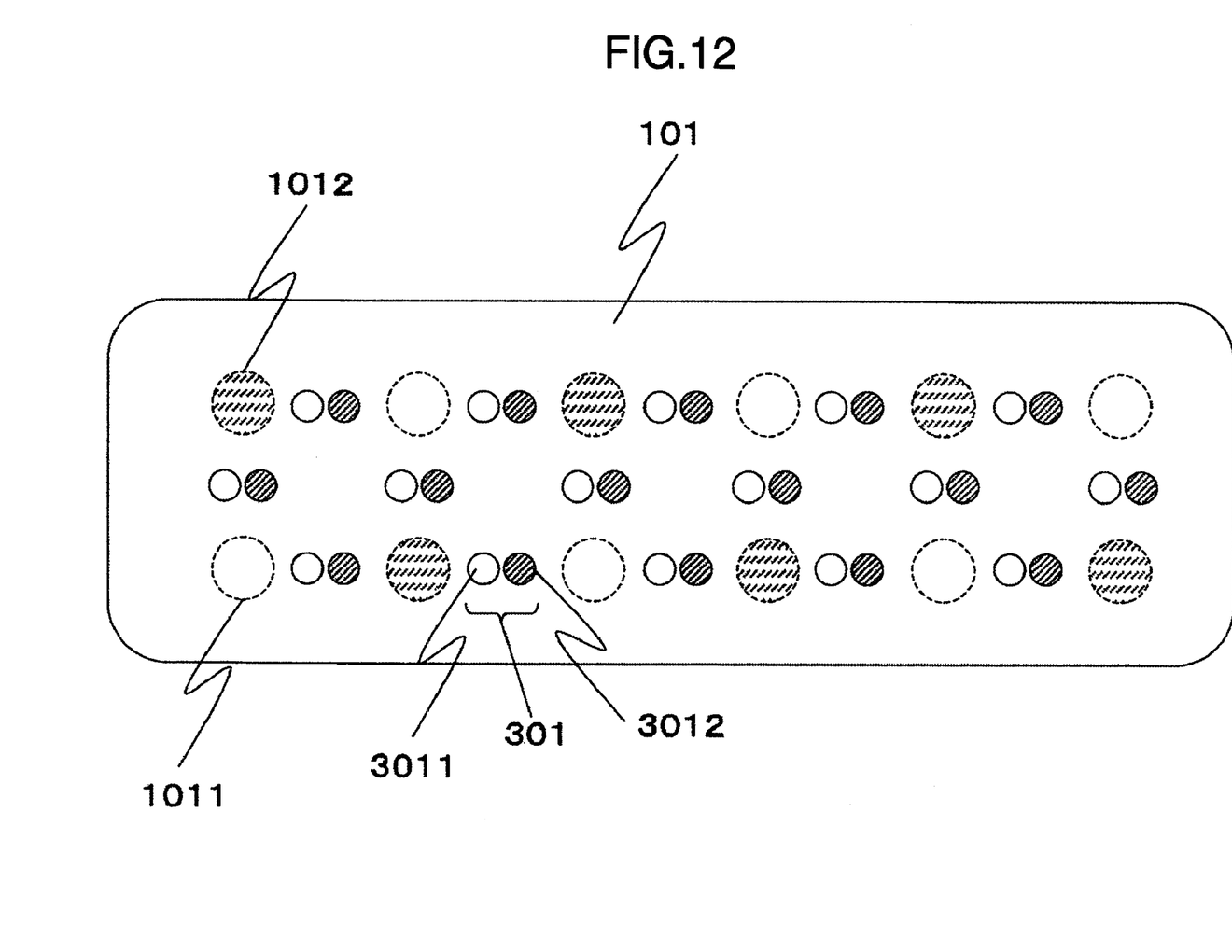
FIG. 12 is a constitution example for displaying living body information on a display part, in the optical measurement instrument for the living body in the present invention.
Figure 13:
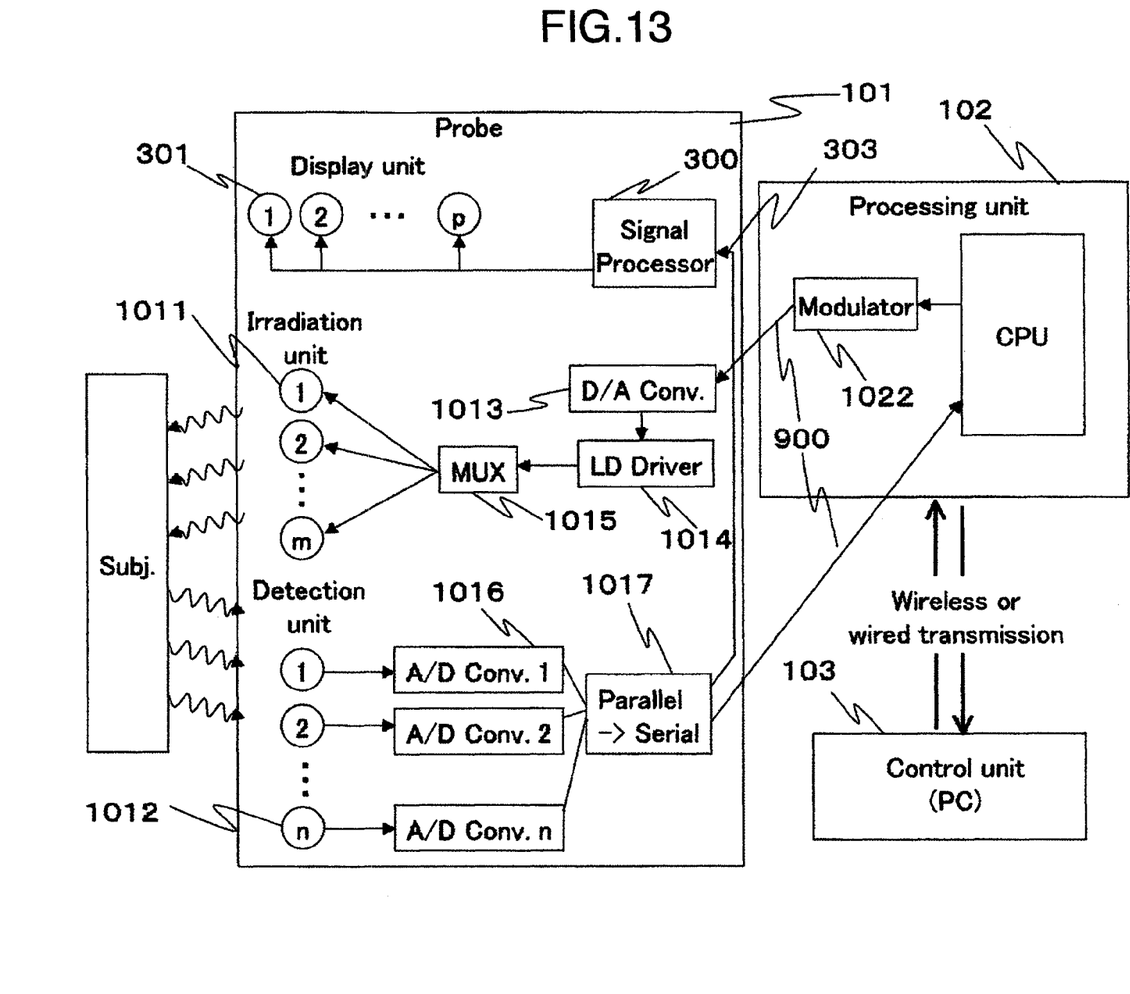
FIG. 13 is a constitution example for displaying living body information on a display part, in the optical measurement instrument for the living body in the present invention.

Then, explanation will be given of an embodiment for instantly displaying measurement results on the probe unit 101, by providing display parts 301 and one processing part 300 in the probe unit 101, as shown in FIG. 11. The living body information processed and acquired by the processing unit 102 is instantaneously transmitted to the processing part 300 by the cable 302 that connects the processing unit 102 and the probe unit 101, and then transmitted to each of the display parts 301 by the processing part 300. The display parts 301 may be visual display instruments such as LED, liquid crystal or the like; voice and sound providing instruments such as a speaker or the like; a vibration instrument such as a vibrator or the like; or a temperature exhibiting instrument using a thermistor or the like. FIG. 12 shows a surface mounting example, in the case where living body information to be displayed is two kinds, and the display parts 301 is provided at the front surface of the probe unit 101, and the irradiation parts 1011 and the light detection parts 1012 at the rear surface thereof. The irradiation parts 1011 and the light detection parts 1012 shown by a broken line represent presence at the rear surface. FIG. 12 shows an example where living body information is acquired at nearly the midpoint of the irradiation parts 1011 and the light detection parts 1012, and the display parts 301 are arranged at a place where living body information is estimated to be acquired, however, the display parts 301 may be surface mounted at a suitable arrangement position, if necessary. Because, in this example, living body information is present in two kinds, the first display parts 3011 for displaying the first living body information, and the second display parts 3012 for displaying the second living body information are present. For example, in the case where the first display parts 3011 and the second display parts 3012 are both LEDs and are display parts for showing concentrations of two kinds of specific substances in the living body, as the living body information, by increasing emission power with increase in the concentrations of the substances, or by decreasing emission power with decrease in the concentrations of the substances, concentration change of each substance, as living body information, can be instantaneously displayed. In addition, as shown in FIG. 13, the display parts 301 can be controlled by a cable 303, which is provided inside the probe unit 101, as a substitution for the cable 302, so as to transmit signals, acquired by the light detection parts 1012, to the processing part 300 without passing through the processing unit 102, and subjecting to processing necessary to acquire living body information, at the processing part 300.

The optical measurement instrument for the living body, according to the present invention, is proposed and realized not only to remove an optical fiber, used in a conventional optical measurement instrument for the living body, but also to make compact sizing of a practical instrument, by instrument constitution characterized by being provided with the digital-to-analog converter, the driving device for a light source, the multiplexer, the analog-to-digital converter and the parallel-serial converter, inside the probe unit. With compact sizing, restriction for the subject is reduced, which makes it possible to realize utilization in wide fields including not only special agencies such as medical and welfare agencies or research agencies, but also sports or amusement and education and the like.

It should be further understood by those skilled in the art that although the foregoing description has been made of embodiments of the invention, the invention is not limited thereto and various changes and modifications may be made without departing from the spirit of the invention and the scope of the appended claims.

The invention claimed is:

1. An optical measurement instrument for a living body, the optical measurement instrument comprising:
a probe unit including a plurality of light irradiation parts for irradiating light onto a subject, and a plurality of light detection parts for detecting light transmitting through or reflecting from the inside of said subject; and
a processing and control unit adapted to transmit a signal for light modulation on light to be emitted from each of said light irradiation parts to said probe unit, and to receive a measurement result corresponding with received light signals from said probe unit,
wherein said probe unit further comprises, inside thereof:
at least one driving device configured to receive said signal for light modulation and to output a driving signal which is modulated depending on said signal for light modulation and is to be sequentially distributed to each of said light irradiation parts;
a multiplexer for timewise and sequentially distributing said driving signal to each of said light irradiation parts to make each of said light irradiation parts sequentially emit light involving an intensity modulation;
a plurality of analog-to-digital converters respectively configured to convert respective light detection signals detected at said light detection parts into digital signals; and
a parallel-serial converter configured to convert the light detection signals that were respectively converted to the digital signals into a serial signal that is sequentially indicating each of light values respectively detected at said light detection parts and to transmit the serial signal to said processing and control unit as the measurement result.

2. The optical measurement instrument for the living body according to claim 1, wherein said probe unit further comprises, inside thereof:
a monitor photodiode in each of said light irradiation parts for monitoring intensity of light irradiated onto the subject at said each light irradiation part; and
another analog-to-digital converter configured to convert a monitoring signal emitted at said monitor photodiode in said each light irradiation part, from an analog signal to a digital signal;
wherein said monitoring signal is transmitted to said processing and control unit and said light detection signal that was transmitted from each of said light detection parts to said processing and control unit is divided by said monitoring signal emitted at said monitor photodiode in said each light irradiation part.

3. The optical measurement instrument for the living body according to claim 1, wherein said probe unit further comprises, inside thereof:
a monitor photodiode in each of said light irradiation parts for monitoring intensity of light irradiated onto the subject at said each light irradiation part; and
another analog-to-digital converter configured to convert a monitoring signal emitted at said monitor photodiode in said each light irradiation part, from an analog signal to a digital signal;
wherein intensity of light emitted at said each light irradiation part is maintained nearly constant, by transmitting said monitoring signal to said processing and control unit, and adjusting said signal for light modulation based on said monitoring signal emitted at said monitor photodiode in said each light irradiation part.

4. The optical measurement instrument for the living body according to claim 1, wherein said probe unit further comprises, inside thereof:
a plurality of multiplexers which are configured to receive said driving signal from said at least one driving device and to share burden to sequentially distribute said driving signal to said light irradiation parts.

5. The optical measurement instrument for the living body according to claim 1, wherein said probe unit further comprises, inside thereof:
a plurality of driving devices configured to output a plurality of driving signals and a plurality of multiplexers;
wherein signal for light modulation, each having different modulation frequencies or codes, are transmitted to each of a plurality of said driving devices, and said driving signals, which are respectively modulated depending on said signals for light modulation, each having different modulation frequencies or codes, are transmitted to each of said multiplexers.

6. An optical measurement instrument for a living body, the optical measurement instrument comprising: a probe unit including a plurality of light irradiation parts for irradiating light onto a subject, and a plurality of light detection parts for detecting light transmitting through or reflecting from the inside of said subject; and a processing and control unit adapted to transmit a signal for light modulation on light to be emitted from each of said light irradiation parts to said probe unit, and to receive a measurement result corresponding with received light signals from said probe unit; wherein said probe unit further comprises, inside thereof: at least one driving device configured to receive said signal for light modulation and to output a driving signal which is modulated depending on said signal for light modulation and is to be sequentially distributed to each of said light irradiation parts; wherein light irradiated at each of said light irradiation parts is emitted independently timewise and subjected to intensity modulation, said measurement result is transmitted as a serial signal to said processing and control unit, and said processing and control unit is configured to perform a lock-in detection processing of the measurement result.

7. The optical measurement instrument for the living body according to claim 6, wherein said probe unit further comprises, inside thereof:
a multiplexer for timewise and sequentially distributing said driving signal to each of said light irradiation parts to make each of said light irradiation parts sequentially emit light involving an intensity modulation;
a plurality of analog-to-digital converters respectively configured to convert respective light detection signals detected at said light detection parts into digital signals; and
a parallel-serial converter configured to convert the light detection signals that were respectively converted to the digital signals into said serial signal that is sequentially indicating each of light values respectively detected at said light detection parts result.

8. The optical measurement instrument for the living body according to claim 7, wherein said probe unit further comprises, inside thereof:
a monitor photodiode in each of said light irradiation parts for monitoring intensity of light irradiated onto the subject at said each light irradiation part; and
another analog-to-digital converter configured to convert a monitoring signal emitted at said monitor photodiode in said each light irradiation part, from an analog signal to a digital signal;
wherein said monitoring signal is transmitted to said processing and control unit and said light detection signal that was transmitted from each of said light detection parts to said processing and control unit is divided by said monitoring signal emitted at said monitor photodiode in said each light irradiation part.

9. The optical measurement instrument for the living body according to claim 7, wherein said probe unit further comprises, inside thereof:
a monitor photodiode in each of said light irradiation parts for monitoring intensity of light irradiated onto the subject at said each light irradiation part; and
another analog-to-digital converter configured to convert a monitoring signal emitted at said monitor photodiode in said each light irradiation part, from an analog signal to a digital signal;
wherein intensity of light emitted at said each light irradiation part is maintained nearly constant, by transmitting said monitoring signal to said processing and control unit, and adjusting said signal for light modulation based on said monitoring signal emitted at said monitor photodiode in said each light irradiation part.

10. The optical measurement instrument for the living body according to claim 7, wherein said probe unit further comprises, inside thereof:
a plurality of multiplexers which are configured to receive said driving signal from said at least one driving device and to share burden to sequentially distribute said driving signal to said light irradiation parts.

11. The optical measurement instrument for the living body according to claim 7, wherein said probe unit further comprises, inside thereof:
a plurality of driving devices configured to output a plurality of driving signals and a plurality of multiplexers;
wherein signal for light modulation, each having different modulation frequencies or codes, are transmitted to each of a plurality of said driving devices, and said driving signals, which are respectively modulated depending on said signals for light modulation, each having different modulation frequencies or codes, are transmitted to each of said multiplexers.

* * * * *